United States Patent [19]

Haber et al.

[11] Patent Number: 5,352,036

[45] Date of Patent: Oct. 4, 1994

[54] METHOD FOR MIXING AND DISPENSING A LIQUID PHARMACEUTICAL WITH A MISCIBLE COMPONENT

[75] Inventors: Terry M. Haber, Lake Forest; Clark B. Foster, Laguna Niguel; William H. Smedley, Lake Elsinore, all of Calif.

[73] Assignee: Habley Medical Technology Corporation, Laguna Hills, Calif.

[21] Appl. No.: 91,722

[22] Filed: Jul. 12, 1993

Related U.S. Application Data

[63] Continuation of Ser. No. 950,105, Sep. 23, 1992, abandoned.

[51] Int. Cl.⁵ .............................................. B01F 13/08
[52] U.S. Cl. ..................................... 366/130; 206/219;
206/221; 206/818; 215/DIG. 8; 222/1;
222/226; 222/386; 366/273; 366/347; 604/56;
604/82; 604/416; 604/903
[58] Field of Search ............... 604/201, 228, 232, 416,
604/903, 51, 52, 56, 82; 206/219, 221, 818;
215/228, 231, 247, DIG. 3, DIG. 8; 366/129,
130, 273, 274, 342, 602, 347; 222/1, 226, 386;
128/898

[56] References Cited

U.S. PATENT DOCUMENTS

| | | | |
|---|---|---|---|
| 2,184,152 | 12/1939 | Saffir | 206/818 X |
| 2,449,968 | 9/1948 | Smith | 604/416 |
| 2,842,126 | 7/1958 | Brown | 604/201 |
| 2,887,108 | 5/1959 | Kendall | 604/201 X |
| 2,922,419 | 1/1960 | Bednarz | 604/201 |
| 3,206,172 | 9/1965 | Gaska et al. | 366/273 |
| 3,219,318 | 11/1965 | Hershler | 366/273 |
| 3,724,820 | 4/1973 | Bonjour et al. | 366/273 |
| 3,789,670 | 3/1974 | Rosenwald | 366/273 X |
| 3,831,903 | 8/1974 | Harmel, Jr. | 366/273 X |
| 3,985,649 | 10/1976 | Eddelman | 366/273 X |
| 4,214,874 | 7/1980 | White | 366/273 X |
| 4,445,895 | 5/1984 | Marguiles | 604/201 X |
| 4,850,966 | 7/1989 | Grau et al. | . |
| 5,120,135 | 6/1992 | Ullman | 366/273 |
| 5,137,528 | 8/1992 | Crose | 604/232 X |
| 5,207,320 | 5/1993 | Allen | 604/416 X |
| 5,227,138 | 7/1993 | Boyd et al. | 366/273 X |

FOREIGN PATENT DOCUMENTS 1398895  5/1988  U.S.S.R. ............... 366/273

*Primary Examiner*—Timothy F. Simone
*Assistant Examiner*—Charles Cooley
*Attorney, Agent, or Firm*—Townsend & Townsend Khourie & Crew

[57] ABSTRACT

A pharmaceutical mixing container for storing a liquid having at least two factions which tend to separate during storage. A housing has an inner volume and is closed at one end by a septum arrangement and at another end by a slidable sealing member. A magnetizable mixing member is located within the housing and contacts the liquid faction of the pharmaceutical contained within the housing. An external magnet produces a magnetic field which extends within the inner volume and interacts with the mixing element. By manually translating the magnet along the axis of the housing, the mixing member is forcibly moved through the liquid causing turbulent waves which provide thorough admixing for the pharmaceutical constituents. By controlling the pace of movement of the magnet, thorough admixing is provided without causing mechanical damage to delicate constituents, such as crystalline factions found in NPH type insulin.

14 Claims, 3 Drawing Sheets

METHOD FOR MIXING AND DISPENSING A LIQUID PHARMACEUTICAL WITH A MISCIBLE COMPONENT

This is a continuation of patent application Ser. No. 07/950,105, filed Sep. 23, 1992, now abandoned.

BACKGROUND OF THE INVENTION

This invention relates to containers for liquids having a miscible component. More particularly, this invention relates to mixing containers for storing a liquid pharmaceutical.

Containers are known for storing a pharmaceutical having a liquid component and a second component miscible with a liquid component. A typical container of this type is filled with the pharmaceuticals and stored for later use. Some pharmaceutical separate into their individual components when left in storage. For example, liquid NPH insulin has a crystalline faction which must be in solution in order to be effectively administered. During storage in a container, such crystals precipitate out of the liquid solution and must be thoroughly mixed with the liquid faction just prior to administration. Admixture of the crystalline faction and the liquid faction has been achieved in the past in a number of different ways. One such technique is to provide a mixing element which is freely moveable within the container, in a similar manner to the mixing ball found in ordinary aerosol spray cans. This solution has been found to be less than desirable, since the crystalline faction is composed of delicate crystals which should not be ruptured during the mixing process. The use of a freely moveable mixing element within the container, however, has been found to rupture the crystals, which severely impairs the effectiveness of the pharmaceutical. Efforts in the past to provide a pharmaceutical mixing container with a freely moveable mixing element devoid of the above disadvantage have not been successful to date.

SUMMARY OF THE INVENTION

The invention comprises a pharmaceutical mixing container with a controllably moveable element contained therein which is capable of providing relatively gentle mixing action to thoroughly admix separated components in a pharmaceutical without mechanically damaging those components.

A pharmaceutical mixing container for storing a liquid having at least two miscible components includes a housing having a first end, a second end and a wall structure defining an inner volume, the housing preferably having cylindrical geometry. A closure member providing a fluid seal is arranged at the first end of the housing, the closure member preferably including a septum and a retaining band for securing the septum to the first end of the housing. A sealing member is positioned at least partially within the housing, preferably adjacent the second end, and provides a second fluid seal for containing the liquid within the housing. A mixing member is located within the inner volume of the housing, the mixing element preferably comprising a sphere fabricated from a ferrous material so as to be magnetically interactive with a magnetic member. Such a magnetic member is provided with the container, and is formed as a generally annular magnet with an inner circumference which is geometrically conformable with the geometry of the outer wall surface of the container housing. In the preferred embodiment, the housing is cylindrical and the external magnet is an annular ring with an inner diameter slightly larger than the outer diameter of the housing. This permits the magnet to be readily translated along the housing axis without abrading the outer surface of the housing.

In use, the liquid is stored within the container and is admixed prior to administration by imparting motion to the mixing element by manually translating the external magnetic member along the outer surface of the housing. As the magnetic member is translated, the mixing member is forced through the liquid due to the magnetic coupling. Motion of the mixing member through the liquid causes turbulence within the liquid, thereby admixing the constituent ingredients. Since the velocity of the mixing member is controlled by the user, mechanical damage to the constituents being admixed is minimized or eliminated by translating the magnetic member at a gentle pace.

The liquid may be hydraulically withdrawn from the inner volume of the housing by penetrating the system with a needle cannula of a syringe and subsequently operating the syringe. The liquid may also be expelled from the inner volume of the housing by penetrating the septum with a double point needle and forcibly ejecting the liquid using a drive stem coupled to the sealing member and translating the sealing member with the drive stem in the direction of the first end.

While the invention may be employed with a wide variety of miscible pharmaceutical components, it is ideally suited for use with pharmaceutical having a liquid faction and a crystalline faction requiring admixture prior to use. In particular, the manually controllable gentle mixing afforded by the mixing member and the magnet is sufficient to thoroughly admix the constituents without damaging the crystal structure.

For a fuller understanding of the nature and advantages of the invention, reference should be had to the ensuing detailed description taken in conjunction with the accompanying drawings.

DESCRIPTION OF THE PREFERRED EMBODIMENTS

Figure 1:
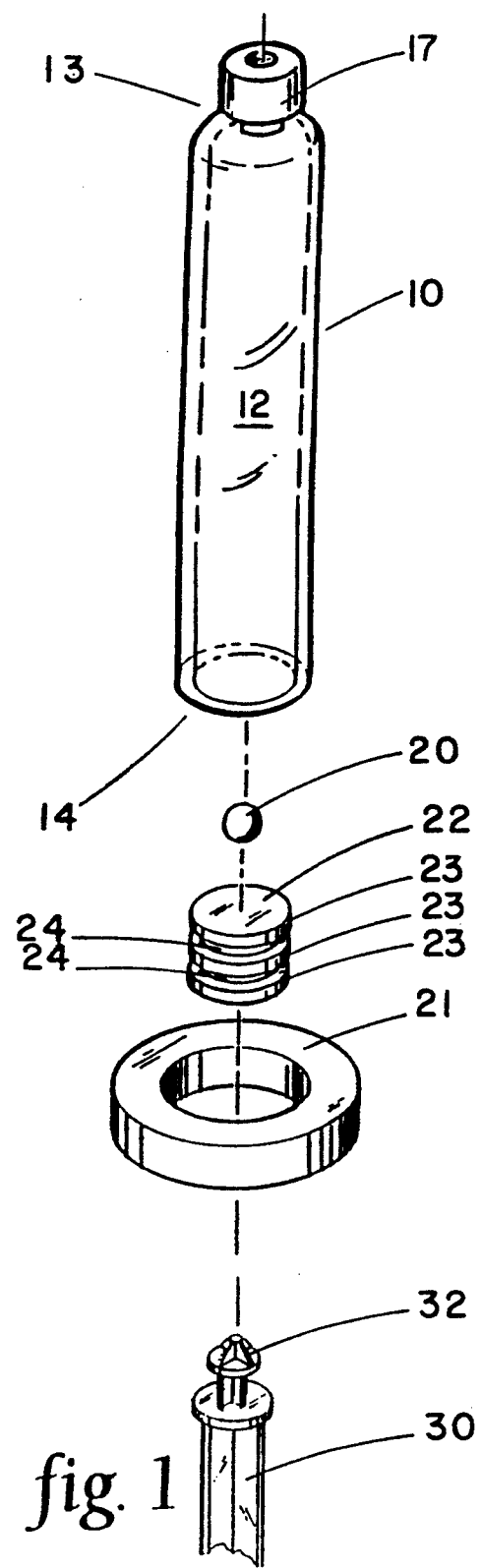
FIG. 1 is an exploded perspective view showing the preferred embodiment of the invention.
Figure 2:
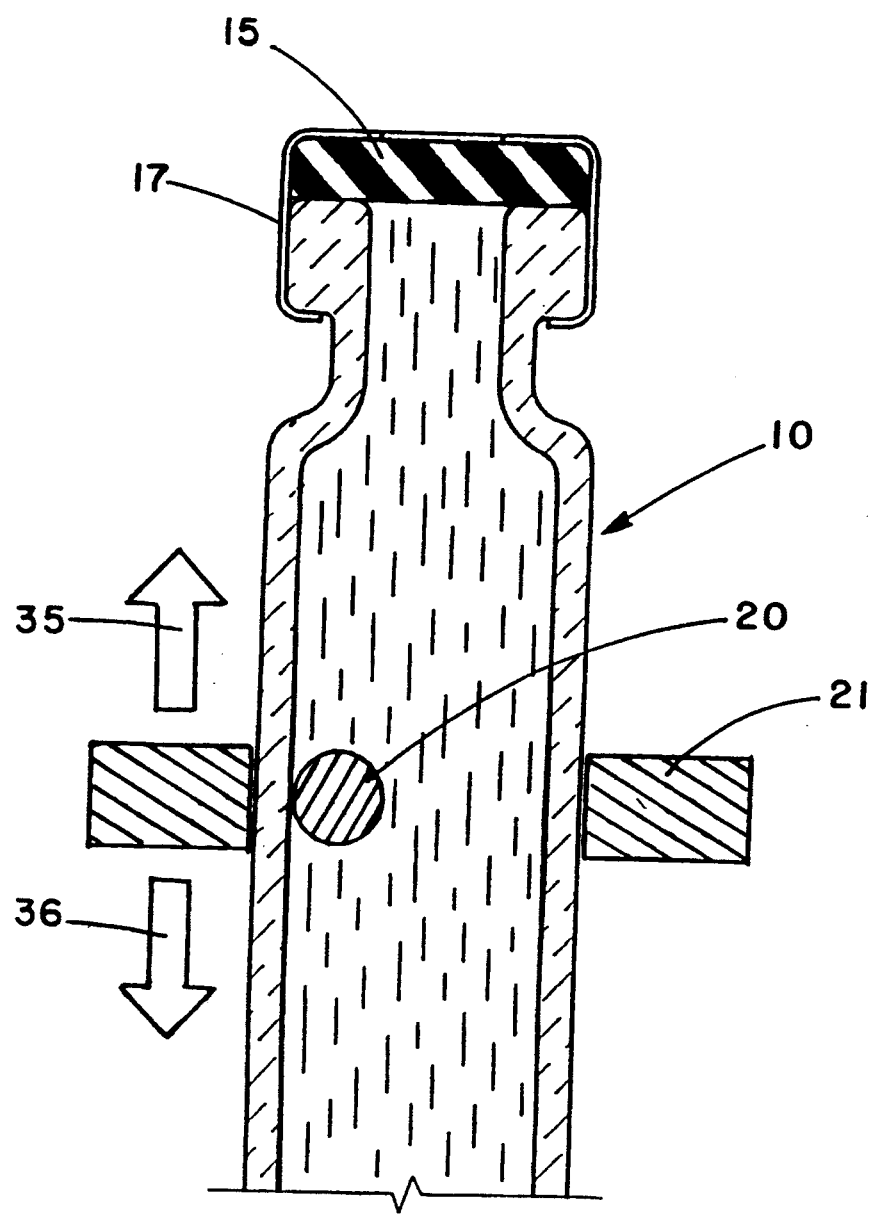
FIG. 2 is a sectional view of the assembled device showing the upper portion of the housing

Turning now to the drawings, FIG. 1 illustrates a preferred embodiment of the invention. As seen in this Fig., a housing generally designated with reference numeral 10 has a generally cylindrical geometrical configuration defining an inner volume 12, a distal end 13 and a proximal end 14. Housing 10 may be fabricated from glass or any suitable plastic material which is compatible with the pharmaceutical to be contained therewithin. Secured to distal end 13 is a closure member comprising an elastomeric septum 15 which is retained to first end 13 by means of a metal band 17. Septum 15 and band 17 are fabricated and arranged in such a manner that access to the inner volume 12 may be gained by penetrating the band 17 and septum 15 with a needle-like probe, such as a needle cannula of a syringe or a double ended syringe needle.

A mixing member 20, shown as a sphere, is contained within inner volume 12. Mixing member 20 may be fabricated from any magnetizable material, such as ferrous oxides, steel rare earth elements, a magnetic agent intermixed with a rubber matrix material or the equivalent. The structure and size of mixing member 20 are selected in such a manner that the member 20 will create sufficient turbulence when moved within container 10 in the manner described below to thoroughly admix the pharmaceutical constituents to be contained within volume 12.

The mixing element 20 is controlled by means of an externally located magnet 21 having an inner surface which is geometrically conformable with the outer surface of container housing 10. In the preferred embodiment, the housing has right circular cylindrical geometry along the major portion of its length, and magnet 21 is an annular ring having an inner diameter slightly larger than the outer diameter of housing 10. Magnet 21 may be fabricated from any suitable permanently magnetizable material, such as a ferrous metal.

A sealing member 22 having an outer diameter providing a sealing engagement with the inner walls of housing 10 is installed adjacent the proximal end 14 of housing 10. Sealing member 22 may be fabricated from a wide variety of suitable materials, such as butyl rubber, silicone rubber or the equivalent. Sealing member 22 functions to provide a fluid seal for the lower end of inner volume 12. To this end, sealing member 22 is provided with a plurality of lands 23 and grooves 24 along the outer surface thereof.

Attached to sealing member 22 is a drive stem 30 for enabling manual expulsion of the liquid within inner volume 12 when the liquid has been admixed and is ready to be dispensed. Drive stem 30 is provided with mechanical coupling element 32, which provides a press fit within a corresponding recess (not shown) within the the hollowed-out interior of sealing member 22. Other mechanical arrangements for coupling drive stem 30 to sealing member 22 will occur to those skilled in the art.

In use, the mixing member 20 is placed within inner volume 12 and sealing member 22 is installed from the proximal end 14 of housing 10. The inner volume 12 is then filled with the pharmaceutical liquid, and septum 15 and closure band 17 are installed to seal volume 12.

When the pharmaceutical is to be administered, the magnet 21 is arranged about the outer surface of housing 10, thereby creating a magnetic field which passes through the interior volume 12. The mixing element is magnetically interactive with the magnetic field: consequently, the position of mixing element 20 with volume 12 can be controlled and changed by sliding magnet 21 along the outer surface of housing 10. The two oppositely facing arrows suggest linear motion along the housing axis in opposite directions. By manually controlling the pace at which magnet 21 is translated, the velocity of mixing element 20 is correspondingly controlled. As mixing element 20 moves through the liquid in volume 12, turbulence is created within the liquid, so that the constituent ingredients are thoroughly admixed.

Figure 3A:
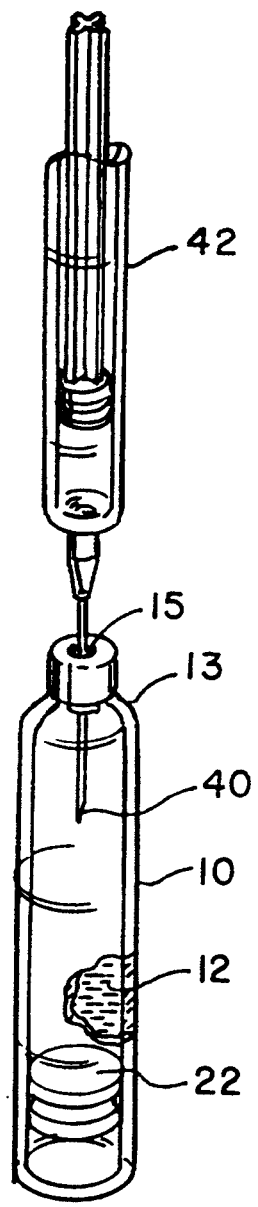
FIG. 3A is a perspective view of a syringe accessing the inner volume of the housing and withdrawing the mixed pharmaceutical.

FIG. 3A shows a syringe 42 with a needle cannula 40 penetrating septum 15 into interior 12 of housing 10. As syringe 42 withdraws a volume of the now mixed liquid pharmaceutical, sealing member 22 moves towards first end 13.

Figure 3B:
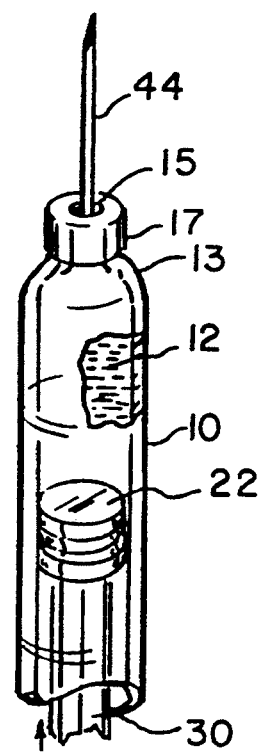
FIG. 3B is a sectional view of the upper portion of the housing and a double point needle dispensing the mixed pharmaceutical.

FIG. 3B shows a double point needle 44 mounted to first end 13 of housing 10 so that one point of needle 44 extends into interior 12 of housing 10 and the opposite point projects out of housing 10. By forcing drive stem 30 upwards towards first end 13, the mixed pharmaceutical is driven out of housing 10 and dispensed through the tip of double point needle 44.

As will now be apparent, the magnet and mixing members are capable of providing thorough admixture of the pharmaceutical constituent ingredients in a relatively simple and expedient fashion. In addition, the container fabricated according to the invention is relatively simple and inexpensive to manufacture, can be readily filled with the appropriate liquid pharmaceutical, and can easily be employed for administering the pharmaceutical to a patient.

While the above provides a full and complete disclosure of the preferred embodiments of the invention, various modifications, alternate constructions and equivalents may occur to those skilled in the art. For example, while mixing member 20 has been illustrated as a sphere, other geometries may be employed, as desired. Further, although magnet 21 has been illustrated and described as an annular ring, other geometrical shapes can be employed, if desired. For example, a partial annulus or a bar magnet may be suitable for some applications. In addition, other mechanical arrangements may be used to provide the translatory motion for sealing member 22 when it is desired to expel the liquid from inner volume 12. Also, the slidable sealing member 22 may be omitted in some applications and the inner volume 12 may be sealed by a solid housing bottom wall or a wall formed internally of the housing walls. Therefore, the above descriptions should not be construed as limiting the scope of the invention, which is defined by the appended claims.

What is claimed is:

1. A method of mixing and dispensing a liquid pharmaceutical having a liquid and a miscible component comprising the following steps:

provinding a pharmaceutical container containing the liquid pharmaceutical with miscible component, the container having a first end, a second end and a wall structure defining an inner volume, the first end including a needle-pierceable member, the container including a magnetic mixing member within the inner volume;

positioning a magnetic field generating element external to the container;

moving the magnetic field generating element such that the magnetic mixing member is translated along the container to admix the miscible component within the liquid pharmaceutical;

controlling the relative velocity between the container and the magnetic field generating element such that the magnetic mixing member will create enough turbulence to thoroughly admix the miscible component within the liquid pharmaceutical without mechanically damaging the miscible component;

accessing the inner volume of the container through the needle-pierceable member by inserting the tip of a needle through the needle-pierceable member; and withdrawing a volume of the now mixed liquid pharmaceutical with miscible component from the container through the needle.

2. The method of claim 1 wherein the providing step is carried out using an elastomeric septum as the needle-pierceable member.

3. The method of claim 2 wherein the providing step is carried out using a retaining band securing the elastomeric septum to the first end.

4. The method of claim 2 wherein the accessing step is carried out by inserting an end of a double ended syringe needle through the septum.

5. The method of claim 4 wherein the providing step includes the step of providing the container with a piston slidably housed within the container and wherein the withdrawing step is carried out by propelling a drive stem coupled to the piston such that said volume is urged out of the container through the double ended syringe needle.

6. The method of claim 2 wherein the accessing step is carried out by inserting the tip of a needle cannula of a syringe through the septum.

7. The method of claim 6 wherein the withdrawing step is carried out by drawing said volume into the syringe through the tip of the needle cannula.

8. The method of claim 1 wherein the providing step is carried out using a spherical magnetic mixing member.

9. The method of claim 1 wherein the providing step is carried out using a generally cylindrical glass pharmaceutical container.

10. The method of claim 1 wherein the positioning step is carried out by positioning an annular permanent magnet external to the container.

11. The method of claim 1 wherein the positioning step includes the step of selecting an annular permanent magnet having an inner surface that is geometrically conformable with an outer surface of the pharmaceutical container.

12. The method of claim 1 wherein the providing step is carried out using insulin as the liquid pharmaceutical with miscible component.

13. A method of mixing and dispensing liquid insulin, the insulin having a miscible component and a liquid component comprising the following steps:

providing a pharmaceutical container containing the liquid insulin, the container having a first end, a second end and a wall structure defining an inner volume, the first end including an elastomeric septum, the container including a magnetic mixing member within the inner volume and a piston slidably housed within said container;

positioning a magnetic field generating element external to the container;

moving the magnetic field generating element such that the magnetic mixing member is translated along the container to admix the miscible and liquid components of the liquid insulin;

controlling the relative velocity between the container and the magnetic field generating element such that the magnetic mixing member will create enough turbulence to thoroughly admix the miscible and liquid components of the liquid insulin without mechanically damaging the miscible component;

accessing the inner volume of the container through the elastomeric septum by inserting an end of a double ended syringe needle through the elastomeric septum; and dispensing a volume of the now mixed liquid insulin from the container by forcing a drive stem against the piston such that said volume of the liquid insulin is urged out of the container through the double ended syringe needle.

14. A method of mixing and dispensing liquid insulin, the insulin having a miscible component and a liquid component comprising the following steps:

providing a pharmaceutical container containing the liquid insulin, the container having a first end, a second end and a wall structure defining an inner volume, the first end including an elastomeric septum, the container including a magnetic mixing member within the inner volume;

positioning a magnetic field generating element external to the container;

moving the magnetic field generating element such that the magnetic mixing member is translated along the container to admix the miscible and liquid components of the liquid insulin;

controlling the relative velocity between the container and the magnetic field generating element such that the magnetic mixing member will create enough turbulence to thoroughly admix the miscible and liquid components of the liquid insulin without mechanically damaging the miscible component;

accessing the inner volume of the container through the elastomeric septum by inserting the tip of a needle cannula of a syringe through the elastomeric septum; and withdrawing a volume of the now mixed liquid insulin from the container by drawing said volume into the syringe through the tip of the needle cannula; and dispensing at least a portion of the liquid insulin from the syringe.

* * * * *